US011707367B2

(12) United States Patent
Messner et al.

(10) Patent No.: US 11,707,367 B2
(45) Date of Patent: Jul. 25, 2023

(54) METHOD FOR CONFIGURING A MYOELECTRICALLY CONTROLLED PROSTHESIS SYSTEM AND PROSTHESIS SYSTEM

(71) Applicant: Otto Bock Healthcare Products GmbH, Vienna (AT)

(72) Inventors: Christoph Messner, Vienna (AT); Sebastian Amsuess, Vienna (AT); Georg Brandmayr, Vienna (AT); Martin Wehrle, Vienna (AT); Markus Friedrich, Vienna (AT); Johannes Steininger, Gaubitsch (AT)

(73) Assignee: Otto Bock Healthcare Products GmbH, Vienna (AT)

( * ) Notice: Subject to any disclaimer, the term of this patent is extended or adjusted under 35 U.S.C. 154(b) by 607 days.

(21) Appl. No.: 16/407,170

(22) Filed: May 8, 2019

(65) Prior Publication Data
US 2019/0343661 A1    Nov. 14, 2019

(51) Int. Cl.
*A61F 2/72* (2006.01)
*A61B 5/00* (2006.01)
(Continued)

(52) U.S. Cl.
CPC .............. *A61F 2/72* (2013.01); *A61B 5/256* (2021.01); *A61B 5/273* (2021.01); *A61B 5/296* (2021.01);
(Continued)

(58) Field of Classification Search
CPC .............................. A61F 2/72; A61F 2002/769
(Continued)

(56) References Cited

U.S. PATENT DOCUMENTS 5,341,813 A * 8/1994 Teare .................... A61B 5/389
                                                              600/546
8,591,599 B1 * 11/2013 Kaliki .................. A61B 5/296
                                                              623/25
(Continued)

FOREIGN PATENT DOCUMENTS

CN        1582866 A      2/2005
CN      101069659 A      5/2007
(Continued)

OTHER PUBLICATIONS

International Preliminary Report on Patentability issued in International Application No. PCT/EP2019/061796, dated Jul. 25, 2019, 9 pgs.
(Continued)

*Primary Examiner* — David H Willse
(74) *Attorney, Agent, or Firm* — Holland & Hart LLP

(57) ABSTRACT

A method for configuring a myoelectrically controlled prosthetic system with a prosthesis socket and several lead electrodes for recording electric muscle activities, featuring the steps: placement of a surface electrode arrangement comprising several surface electrodes around the circumference of a residual limb, recording of electric muscle activity in muscles of the residual limb as electromyograhic signals, the activity being recorded by the surface electrodes, evaluation of the myoelectric signals with regards to the distinctness of the signals, selection of the control procedure that is to be used to control the prosthesis system, based on the evaluation of the distinctness of the signals, and fixing of the lead electrodes to the prosthesis socket.

22 Claims, 7 Drawing Sheets

(51) Int. Cl.
*A61F 2/54* (2006.01)
*A61F 2/80* (2006.01)
*A61B 5/296* (2021.01)
*A61B 5/316* (2021.01)
*A61B 5/273* (2021.01)
*A61B 5/397* (2021.01)
*A61B 5/256* (2021.01)
*A61F 2/76* (2006.01)

(52) U.S. Cl.
CPC .............. *A61B 5/316* (2021.01); *A61B 5/397* (2021.01); *A61B 5/4851* (2013.01); *A61B 5/6811* (2013.01); *A61F 2/54* (2013.01); *A61F 2/80* (2013.01); *A61B 2562/0209* (2013.01); *A61B 2562/043* (2013.01); *A61F 2002/769* (2013.01)

(58) Field of Classification Search
USPC .......................................................... 623/25
See application file for complete search history.

(56) References Cited

U.S. PATENT DOCUMENTS

| | | |
|---|---|---|
| 8,828,093 B1 | 9/2014 | Kuiken |
| 9,566,016 B2 | 2/2017 | Brandmayr et al. |
| 2007/0265711 A1 | 11/2007 | Klein |
| 2009/0216339 A1 | 8/2009 | Hanson et al. |
| 2014/0031952 A1 | 1/2014 | Harshbarger et al. |
| 2019/0059774 A1* | 2/2019 | Barnes .................. A61H 3/00 |

FOREIGN PATENT DOCUMENTS

| | | |
|---|---|---|
| DE | 202006007460 U1 | 10/2007 |
| DE | 102008036714 A1 | 2/2010 |
| DE | 102009056466 A1 | 6/2011 |
| RU | 2635632 C1 | 12/2016 |
| WO | 2018/111138 A1 | 6/2018 |
| WO | 2018026842 A1 | 8/2018 |

OTHER PUBLICATIONS

Written Opinion of the International Searching Authority issued in International Application No. PCT/EP2019/061796, dated Jul. 25, 2019, 8 pgs.

* cited by examiner

METHOD FOR CONFIGURING A MYOELECTRICALLY CONTROLLED PROSTHESIS SYSTEM AND PROSTHESIS SYSTEM

TECHNICAL FIELD

The invention relates to a method for configuring a myoelectrically controlled prosthesis system with a prosthesis socket and several lead electrodes for recording electric muscle activities. The invention also relates to a prosthesis system with a prosthesis socket, which can be arranged on a residual limb; several lead electrodes for recording electric muscle activities; a control unit that is connected to the lead electrodes and a driven prosthesis component, which is fixed to the prosthesis socket and coupled with the control unit. Further aspects of the invention relate to a surface electrode arrangement, surface and/or lead electrodes, a safety element and a cover for a surface electrode arrangement.

BACKGROUND

Prostheses act as replacements for missing limbs. In addition to purely aesthetic aspects, it is desirable for the prosthesis to be able to perform as many of the functions of the missing limb as possible in order to make everyday activities easier for the patient. With lower limb prostheses, prosthesis components are often fixed to a remaining limb or a residual limb via a prosthesis socket. There are different ways to achieve this, such as using a belt system or a negative pressure system and/or a liner system featuring mechanical locking elements at the distal end of the liner. A joint is often arranged distally on the prosthesis socket in order to flexibly connect a further prosthesis component, such as a prosthetic knee joint or a prosthetic ankle joint. With lower limb prostheses, the joints may be designed as locking joints, joints which have been set a single time with regard to their dampening behavior, sensor-controlled passive joints whose dampening behavior can be adjusted via the respective motion sequence, or motor-driven joints. The configurations of upper limb prostheses also range from purely aesthetic prostheses or pulley-activated gripping devices, to motor-driven prosthetic hands that are fixed to upper arm sockets via an elbow joint on the patient.

For driven prostheses it is necessary to control the drive systems very precisely so that the respective prosthesis component performs the desired or required movement. Control may be performed by way of a healthy limb, similar to a remote control system. To this end, sensors are arranged on a healthy limb and movement signals are recorded. A control command for each drive is allocated to each sensor signal. If a certain movement is executed and a sensor signal detected, a command is transmitted to the drive via the control stored in a computer; this command instructs that a certain shift or swiveling is to be executed across a particular path in a particular time.

Alternatively, it is possible to use electrodes to record a patient's biosignals, such as electric muscle activity caused by muscle contractions. These signals are recorded as electromyographic signals and can be used to control one or several drives. Thanks to learned contraction patterns, a patient is able to get the prosthesis component to perform different actions by contracting one or several muscles. Two electrodes, via which a so-called dual channel treatment can take place, often suffice for this purpose. A gripper device can be easily opened and closed via a simple signal sequence.

Complex prosthetic treatments, for example with a driven prosthetic elbow device on a prosthetic hand with individually adjustable prosthetic fingers and/or a wrist that can be flexed and/or rotated, cannot be controlled by a patient on an everyday basis using a dual channel control system. For the control of such a complex treatment, eight or more pairs of electrodes are required to be able to execute an allocation of many myoelectric signals via pattern recognition and from this, to derive a correspondingly complex control system.

Following the loss of a limb, patients should receive a prosthetic treatment as quickly as possible in order to make optimal use of the muscles that are still available, as well as avoiding the situation in which a patient adapts to life without a limb. In this case, it can be problematic that in the event of amputation, the wound has to heal and that swellings or bruisings must heal, meaning that it is not possible to adjust a final prosthesis socket. Furthermore, with a new patient who is to be treated with a prosthesis, it is difficult to predict the type of treatment possible.

US 2014/0031952 A1 relates to methods and systems for connecting physiological devices to a prosthesis system. To this end, a number of different types of physiological activity signals are received from the user; an intended movement is then decoded on the basis of each type of signal. The intended movements are bundled to create a joint decision in order to control movable elements of the prosthetic device.

DE 10 2009 056 466 A1 relates to a system and method for the adaptive control and regulation of a prosthesis with an intuitive control, wherein a number of muscle activity signals in a muscle of a wearer of a prosthesis are measured. At the same time, information on an actual state of movement of the wearer of the prosthesis is measured; this information is then used to define a possible current state of movement. With the aid of a method for detecting signal patterns, the muscle activity signals are used to extract muscle activity properties. With the aid of the current state of movement, the extracted muscle activity properties are used to determine at least one intuitive signal. The intuitive signal is used to evaluate and/or regulate and/or control an actuator of the prosthesis.

US 2009/0216339 A1 relates to a system for conducting myoelectric signals through a liner of a prosthetic device. A flexible conductive electrode insert defines an initial region that is arranged on an inner surface of the liner and touches the skin of the user. A second region extends through the liner, a third region extends on the outer surface of the liner. An adhesive is used to fix at least the second and third region of the insert to the liner.

DE 10 2008 036 714 A1 relates to a method for visualizing multi-channel sensor signals, especially myoelectric signals, which are derived via electrodes from a limb or a residual limb. A display direction and display value are allocated to every sensor signal. The display direction represents precisely one sensor signal, the display value represents the intensity of the respective signal. The display direction and the indicator value of all sensor signals are simultaneously depicted in real-time on a display device as a graphic object.

WO 2018/026842 A1 relates to a technology for signal processing, by means of which intended limb movements are derived from intra-muscular or surface electromyographic signals. Electromyographic signals are recorded by an electrode array and conveyed to a processor, which is connected to a memory. The electromyographic data are associated with a training movement, which is performed by a user in response to a training movement request. Using the single-ended channels, differential channel pairings are determined and characteristic data properties extracted. The characteristic data properties are allocated to the movement request. A set of characteristic data properties is selected as a training input in a decoding model, which is configured to correlate the characteristic property data set with the intended movement. The decoding model is configured in such a way that it uses the characteristic data model.

SUMMARY

The object of the present invention is to provide a method for configuring a myoelectrically controlled prosthesis system and a prosthesis system as such, by means of which it can be determined as quickly as possible which treatment is available for the patient and the best way to configure the prosthesis system.

The method for configuring a myoelectrically controlled prosthesis system with a prosthesis socket and several lead electrodes for recording electric muscle activities first stipulates the placement of a surface electrode arrangement, comprised of several surface electrodes, around the circumference of a residual limb. By way of the surface electrodes of the surface electrode arrangement, electric muscle activity in muscles of the residual limb are recorded as electromyographic signals. The electromyographic signals are evaluated in terms of their signal quality. On the basis of the evaluation of the signal quality, the control procedure is selected by means of which the prosthesis system is to be controlled. The lead electrodes are then fixed to the prosthesis socket. Thanks to the surface electrode arrangement, it is possible to record electromyographic signals and evaluate them in terms of a signal quality, without requiring a prosthesis socket to already be equipped with lead electrodes. Signal quality should be understood to mean, amongst other things, the separability of the signals, in particular the form or the course of the signal or the point at which the signal is recorded. Furthermore, the reproducibility of the signal is a quality criteria: a high signal quality is achieved when the signal always appears the same, i.e. when a patient is able to produce the same signal. The sustainability of the signal is relevant for the signal quality: when the signal can be produced and relayed for a longer period of time, it is better than a short signal, which could, where applicable, be interpreted as a disturbance and not taken into account. To this end, the patients who have the surface electrode arrangement are requested to perform muscle activities, such as performing the activity that should be performed by the prosthesis device, such as opening a hand, closing a hand, rotating a wrist or flexing the hand. Of course, this activity cannot be performed immediately by the patient, as the limb which is replaced by the prosthesis is missing; however, the remaining muscles can be activated as they were prior to the loss of the limb. This results in electronic potentials, which are recorded by surface electrodes and transferred to an evaluation unit or control unit. Using, for example, the signal duration, the signal intensity, the edge steepness or a signal frequency during muscle contractions, it is possible to determine whether a complex electronic control of a prosthesis device is at all possible. These properties of the signals are an integral part of the signal quality that is used to evaluate and decide on the type of control and the type of prosthetic treatment. For instance, if muscles and/or nerves are so badly damaged that the patient is not able to produce any complex, sufficiently clear signals, the treatment for the patient is selected such that a dual channel treatment represents the optimal treatment. If a patient is able to produce a sufficient number of myoelectric signals of sufficient quality with a sufficient degree of distinctiveness, a complex prosthesis treatment with a range of drives and functions can be deliberately controlled by the patient via pattern recognition or another evaluation of the electromyographic signals. Such a patient can then be equipped with a corresponding prosthesis with a prosthesis socket, driven prosthesis components, control units and the like. On the basis of information concerning whether a dual channel treatment or a multi-channel treatment is practical and consequently implemented, the lead electrodes, which may also be designed as surface electrodes, are fixed to the corresponding point of the final prosthesis socket. As a result, the selected control for the drives of the prosthesis device constantly receives signals from the predetermined muscle regions or from the respective muscles, which increases control accuracy and therefore the quality of the performance of the movements by the prosthesis component.

The surface electrode arrangement is preferably designed to be independent from the prosthesis socket and is placed separately from the prosthesis socket in order to arrange the surface electrodes such that they are spread across the circumference of the residual limb. The surface electrodes are applied to the surface of the skin of the residual limb on which the prosthesis is to be arranged, without having to execute a more or less complicated molding of the residual limb for the production of a positive model, on which the prosthesis socket will be modeled using fiber-reinforced plastics. In principle, other methods for producing a prosthesis socket are possible, just as the use of other materials is possible and proposed. The separate arrangement of the surface electrodes from the prosthesis socket via the surface electrode arrangement increases the flexibility of the positioning and also allows for very early examination and determination as to whether a patient is able to produce electromyographic signals, and if so which ones.

The surface electrode arrangement is preferably arranged on the residual limb such that is can be shifted and/or twisted, in order to arrange the surface electrode arrangement at different points of the residual limb when it is in place. The twisting and/or shifting of the surface electrode arrangement on the residual limb enables the recording of the optimal positions of the electrodes. The surface electrode arrangement is twisted and/or shifted until the best possible signals can be produced by the patient, via muscle contractions, and recorded. Specifically, the best possible signals are those which are best-suited on a whole for the control in terms of their signal quality. For this purpose, all signals are observed, meaning that a range of parameters have to be observed and evaluated. For instance, the evaluation may show that in a first position, the amplitude of two signals is not at its maximum, but the edge steepness and the spatial separation of the signals is better than in a second position with maximal amplitudes; the first position is therefore the best position, despite not exhibiting maximum values in the criteria.

The surface electrodes are preferably arranged at an equal distance or for the most part at an equal distance from one another around the residual limb: for example, six electrodes are at a distance of 60° or approximately 60° from one another, 8 electrodes are at a distance of 45° or approximately 45° from one another, and four electrodes are at a distance of 90° or approximately 90° from one another. The electromyographic signals of the surface electrodes are preferably evaluated in terms of their amplitude, duration, frequency and/or range. The evaluation is conducted in terms of its applicability with regards to identifying commands. For example, if it is recognized that only two muscles are able to produce usable myoelectric signals, a treatment can be ruled out that makes use of a prosthesis device which is based on a four-channel control system, such as the control of a prosthetic hand with multiple drives.

An embodiment of the method proposes a selection and definition of a basic configuration of the control procedure, such as the basic configuration which determines that a dual channel control or pattern recognition is conducted, or a basic configuration for an orthopedic technician who then adjusts this configuration to the respective patient. The selection of the control procedure may be done automatically in a controller or a computer on the basis of predetermined criteria, in particular on the basis of the degree to which the electromyographic signals can be evaluated.

An embodiment proposes a personalized or calibrated control to be saved and stored in the controller or computer as a basic configuration, said configuration being based on the identified electromyographic signals of a patient, wherein the configuration cannot be changed by the patient. An embodiment of the invention proposes the identification of the two most effectively separated electromyographic signals that are recorded by the surface electrodes, and the use of said signals to decide which type of control is to be used. These two best signals are used as guide signals.

An embodiment of the invention proposes the shifting and/or twisting of the surface arrangement on the residual limb into an end position, wherein at least two electromyographic signals must be detectable in the end position. The detectability is ensured, for instance, when there is a sufficiently large distance with regard to the predetermined criteria for the signal quality. The lead electrodes, which are fixed in the prosthesis socket, are then fixed to the prosthesis socket correspondingly to the end position. The arrangement of the electrodes on the prosthesis socket is then executed in such a way that the lead electrodes assume the positions which the corresponding surface electrodes on the surface arrangement occupied when the optimal position of the surface electrode arrangement on the limb or of the surface electrodes on the residual limb was detected and determined via the evaluation. To this end, a strap that has been divided into segments can be used, by means of which it is possible to mark the respective positions on the prosthesis socket so passage openings can be inserted into the socket.

An embodiment of the invention proposes the fixing of the lead electrodes via a dome bolt connection on the prosthesis socket. When providing a patient with a treatment, an orthopedic technician must equip a prosthesis socket with a number of lead electrodes as devices for recording electromyographic signals. A very common treatment nowadays comprises an eight-channel treatment, which requires the bolting of at least 16 electrodes, and if applicable even more additional electrode contacts for grounding purposes, to the prosthesis socket, for example on an inner socket. In this case, it is important to be able to fix the lead electrodes to the respectively desired point with a low degree of assembly complexity, a low structure height and a high quality. So-called suction socket electrodes are known from the prior art, which feature an active amplifier with a housing and integrated contact points. These suction socket electrodes have to be fixed in a recess inside the inner socket. If the suction socket electrodes are moved, a correspondingly large recess must be made in a new inner socket; the position of the amplifier must already be defined during production of the inner socket. In an alternative method, the drilling of a hole in the prosthesis socket is followed by the insertion of a threaded rod of a dome through the hole. A washer is placed on the threaded rod and a nut is put in place. A contact eyelet of an electrode is placed over the threaded rod and fixed via a further nut. The two nuts are tightened against one another using two wrenches. Finally, protruding threaded rods are sanded down. The number of components used renders assembly more difficult and is accompanied by a comparatively large structural height. The sanding off of the threaded rod moves the thread, rendering a re-positioning of the electrodes difficult. An outward electric insulation towards the outer socket is not available, meaning that disruptions may occur during a configuration of a prosthesis outer socket made of carbon material. The use of a dome bolt connection according to the invention considerably simplifies an assembly. Following the insertion of a hole in the socket, a dome electrode with a thread is inserted through the hole and bolted via a dome nut, which features a moisture-proof washer and an electrical contact. This is achieved via a single tool, such as a hexagon key, a square key or, for example, a simple screwdriver. A cap is then clipped onto the dome nut in order to affect an outward electric isolation. This results in a considerably lower structural height. Only one tool is required. The dome with the thread is preferably mushroom-shaped and, where applicable, features projections or fittings on the underside of the head which prevent or complicate a twisting on the surface of the inner socket or the prosthesis socket. As a result, the need for a second tool to secure the dome is negated. The washer secures the dome nut with respect to the dome against inadvertent detachment. Furthermore, a sealing ring can be provided on the outer side of the dome nut, which also secures against inadvertent detachment and the entry of moisture. Following assembly, it is not necessary to further reduce a threaded rod; the domes and dome nuts that have been used can be used again without difficulty. The domes are preferably made of a corrosion-resistant material, such as titanium.

An embodiment of the invention proposes the connection of the lead electrodes to a control unit via cables; the electrodes are also mechanically secured from becoming detached by way of a safety element. The control unit features plug sockets into which the plugs of the respective lead electrodes, which are rigidly mounted on the prosthesis socket, can be plugged. To prevent the plug from detaching during operation of the prosthesis, the safety element is fixed over the plug connector of the control unit, for example it is clipped elastically across the housing of the control unit, such that the backs of the plugs lie flat against the safety element and the cables reach through recesses inside of the safety element. The safety element can secure all the plugs at once.

The prosthesis system with a prosthesis socket, which can be placed on a residual limb, with several lead electrodes for recording electric muscle activities; a control unit that is connected to the lead electrodes and a driven prosthesis component, which is fixed to the prosthesis socket and coupled with the control unit, includes a surface electrode arrangement with several surface electrodes, which can be placed around the circumference of a residual limb, wherein the surface electrode arrangement can be arranged on the residual limb such that it can be shifted and/or twisted.

As a result of the configuration that allows the surface electrode arrangement to be shifted and/or twisted, it is possible to determine the fundamental suitability of a patient for certain prosthesis system or control devices, and configurations of a prosthesis system. Unlike the case with a fixed installation of lead electrodes on a prosthesis socket, such as a prosthetic inner socket, the surface electrode arrangement can be arranged on the residual limb independently from the prosthesis socket, such that it can be shifted and/or twisted. The surface electrodes on the surface electrode arrangement are then able to easily record the electric muscle activity, which can then be processed as electromyographic signals. Rather than training a patient to tense particular muscles in a particular way, the surface electrode arrangement can easily detect an optimal positioning of the surface electrodes and subsequently the lead electrodes. The orientation of surface electrodes on the surface electrode arrangement with respect to the residual limb is recorded and the position of the surface electrode arrangement which has been deemed the optimal position on the residual limb, and thereby also of the surface electrodes on the surface of the residual limb, are subsequently transferred to the prosthesis socket, which positions the lead electrodes to the same points when it is mounted; the prosthesis socket is generally designed as a prosthesis socket which has been individually adjusted to the residual limb, such that a twisting or shifting relative to the residual limb is not possible. When the prosthesis socket is in the set position on the residual limb, the lead electrodes are arranged as definitive electrodes in the positions that were identified as the respective best position by means of the surface electrode arrangement.

The surface electrode arrangement is preferably designed as a sleeve, which can be placed around the residual limb. The surface electrode arrangement or the sleeve may be designed as a closed, circular strap or comprise such a support element, wherein it is preferably designed to be elastic in the circumferential direction. In addition to a configuration of the surface electrode arrangement or sleeve or the support element made of an elastic fabric, it may also be designed to be made of an elastic synthetic material, such as corrugated plastic, wherein the cross-section of the wave shape or wave contour of the surface electrodes runs towards the inward-facing projections or the regions that are closest to the central point of the cross-section or the central axis in the longitudinal direction, i.e. in the proximal-distal direction of the surface electrode arrangement, such that the surface electrodes can maintain good contact with the surface of the skin of the residual limb.

The surface electrodes are preferably arranged on the surface electrode arrangement at an equal distance or for the most part at an equal distance from one another in the circumferential direction, so that the signals can be uniformly applied to a diagram. Markings or labels may be arranged on the surface electrode arrangement, e.g. on the support element, which identify the respective positions of the surface electrodes, for example the positions may be numbered consecutively or allocated consecutive letters.

Particularly in the case of a configuration of the surface arrangement that is designed as a circular or strap-like sleeve or with a circular or strap-like support element with a distal end and a proximal end and at least one proximal insertion opening, it is beneficial for the surface electrode arrangement to have at least one stabilizing element that extends in the proximal/distal direction, in order to prevent a shortening in the proximal/distal direction in the event of an expansion in the circumferential direction. The stabilizing elements can be designed to be rod-like and preferably accommodate the surface electrodes.

A replaceable cover may be arranged on the surface electrode arrangement, said cover being composed of a flexible material, such as a flexible textile. Markings may be arranged on the surface electrode arrangement, e.g. on the support element and/or the cover, in order to be able to conduct the correct allocation of both the surface electrode arrangement to the electrodes and of the cover to the surface electrode arrangement and the electrodes. The cover may be fixed to the surface electrode arrangement via positive-locking elements, such as velcro; alternatively, buttons, hooks etc. may be provided on the surface electrode arrangement in order to fix the cover to it. The interior of the cover is preferably designed to feature recesses for the surface electrodes, so as to enable direct contact between the surface electrode and the surface of the skin of the residual limb. The recesses also prevent a shifting of the cover relative to the surface electrode arrangement during use, as the surface electrodes, which protrude inwards, prevent a twisting or shifting of the cover.

Given that the surface electrode arrangement is designed as a system component that can be placed on the residual limb independently of the prosthesis socket and is preferably only used for installing or configuring the prosthesis, there is no use for the surface electrode arrangement with a final configuration of the prosthesis socket that features fixed lead electrodes. As a result, the surface electrode arrangement can then be returned to the orthopedic technician, who then disposes of the cover and, after proper cleaning, can give the remaining surface electrode arrangement with a new cover to another patient.

A variation of the invention includes the integration and fixing of the surface electrode arrangement in the definitive prosthesis socket; it also stipulates that the surface electrodes form the lead electrodes, which then deliver the electromyographic signals for the control of the driven prosthesis device.

The surface electrodes and/or lead electrodes can be designed as dome bolts with dome nuts and bolted to the surface electrode arrangement or the prosthesis socket. The configuration of the respective electrodes as dome bolts with dome nuts, which are designed to be inserted through a passage opening in the surface electrode arrangement, for example inside the sleeve or the support element, or in the prosthesis socket, a number of electrodes can be simply and quickly fixed in the correct position using a single tool. The configuration of the electrodes as dome bolts with dome nuts allows for a moisture-proof fixing of the electrodes. The dome bolt may comprise an undercut, which enables a high surface pressure in the surrounding area, thereby ensuring that moisture cannot get behind the cap-like contact surface of the dome bolt. Furthermore, a sealing ring can be arranged on the outer side of the bolt nut, which seals the bolt nut against moisture. An additional sealing disc may be provided on the outer side of the surface electrode arrangement or the prosthesis socket, said sealing disc being connected to an electrical contact, such that a moisture-proof fixing of the electrodes on the respective support can be achieved.

An embodiment of the invention proposes that at least one cable is fixed to the prosthesis socket or the surface electrode arrangement such that it can be detached and is in electrical contact with the lead electrode or the surface electrode. The cable is insulated against the surface arrangement or the prosthesis socket; in the same way, the respective electrode is insulated against the environment. This renders signal interference impossible. As a result, it is possible that only the cable that is in electrical contact with the electrode can convey the electromyographic signals to the respective control unit. The control unit can be connected to the lead electrode(s) or the surface electrodes via at least one plug, such that it can be detached. A mechanical safeguard against a detachment against the plugging direction of the plug in the form of a safety element is proposed in an embodiment, which proposes, for example, a recess in the safety element for the respective cable. The dimensions of the recess are configured in such a way that the back of the plug lies flat against the safety element, so that when the safety element is securely fixed to the control unit, for instance via an elastic snap device or a positive-locking element, the respective cable is mechanically secured.

The invention also relates to a surface electrode arrangement, especially in the form of a sleeve, as described above. The invention also relates to an electrode, especially in the form of a surface electrode or lead electrode, as described above. The invention also relates to a safety element like the one described above.

BRIEF DESCRIPTION OF THE DRAWINGS

In the following, examples of embodiments of the invention will be explained in more detail by way of the attached drawings.

They show.

DETAILED DESCRIPTION

Figure 1:
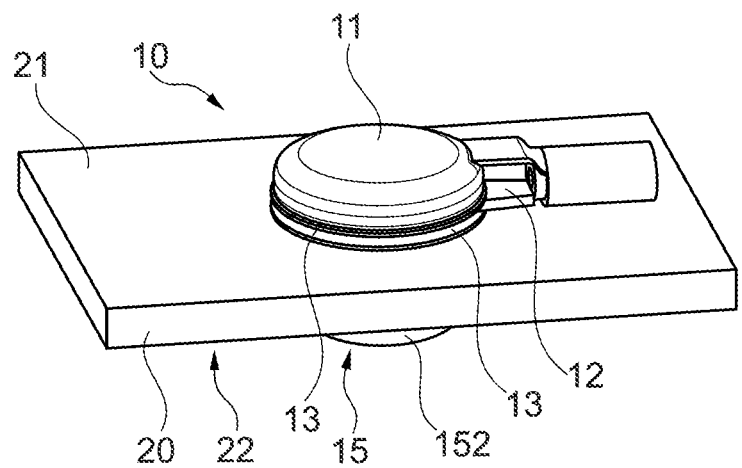
FIG. 1—a complete view of a lead electrode.

FIG. 1 shows a perspective depiction of an assembled electrode in the form of a lead electrode 10, which is mounted to a base body in the form of a prosthesis socket 20. On an outer side 21 facing away from the patient, the lead electrode 10 is covered by an insulating cap 11, which prevents signals that are predominantly taken from the surface of the skin or from the patient from being conveyed to the wrong places or from being compromised by interfering signals. The cap 11 is arranged around a contact tab 12; the contact tab 12 is in turn arranged between two discs 13, which act as electric insulation against the prosthesis socket 20 and also as a seal of a passage spot through the prosthesis socket 20. The contact tab 12 is clamped between the two discs 13; like the contact tab 12, the discs 13 feature a passage opening, through which a dome nut—not visible—is inserted. On an inner side 22 facing the patient, the dome nut is bolted with a dome bolt 15, which comprises a shaft with an outer thread and a head, the so-called dome 152. The dome is in direct contact with the surface of the patient's skin.

Figure 2:
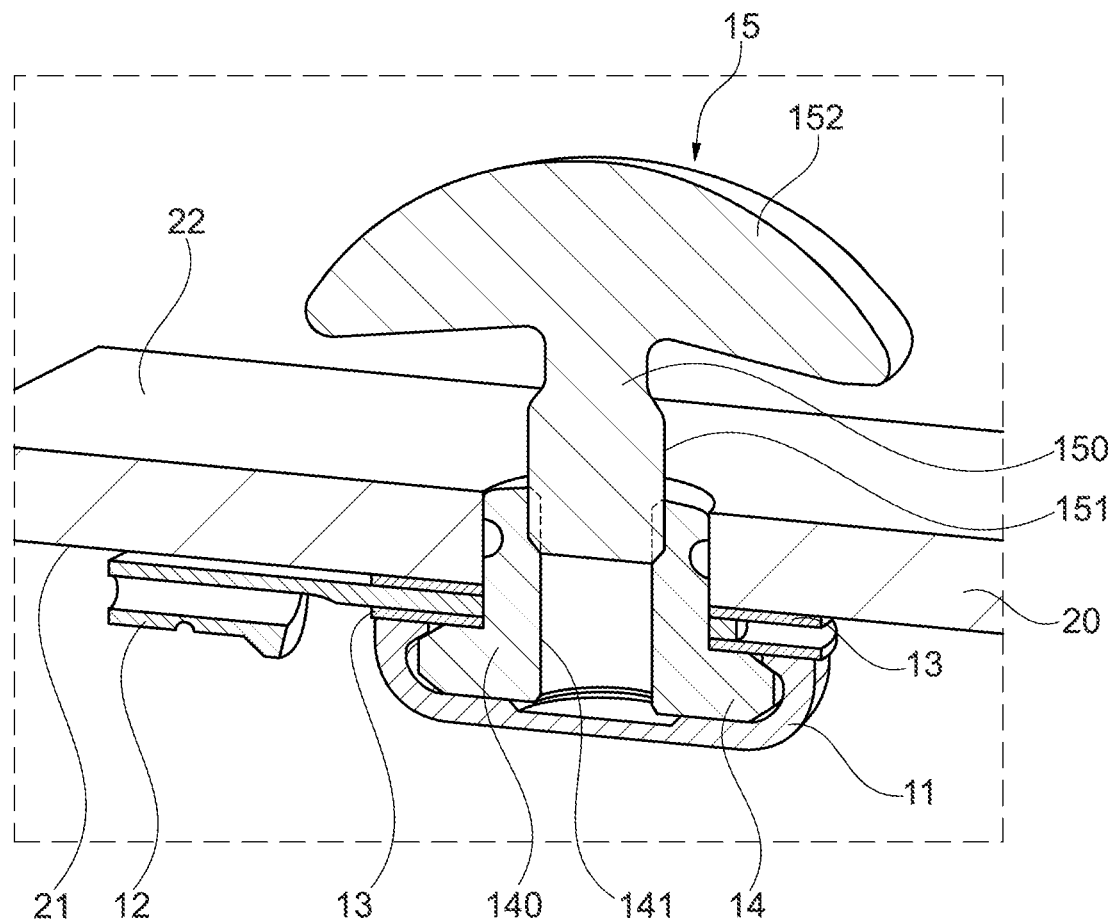
FIG. 2—a sectional view of a lead electrode prior to assembly.

FIG. 2 depicts the construction of the lead electrode 10 in a partially assembled state. The contact tab 12 is arranged between the two discs 13; the dome nut 14 is inserted through a passage opening 23 in the prosthesis socket 20. The cap 11 is already clipped onto the head of the dome nut 14. The dome nut 14 features an inner thread 141, which is arranged in a shaft 140 of the dome nut 14. The shaft 140 extends from the head of the dome nut 14 towards the inner side 22 of the prosthesis socket 20. Furthermore, the shaft 140 has a surrounding groove 142 on the outer side, in which a sealing element can be arranged, such as a closed sealing ring. The outer diameter of the shaft 140 essentially corresponds to the inner diameter of the passage opening 23. In the example of an embodiment shown, the dimensions of length of the shaft 140 are such that it is fundamentally flush with the surface on the inner side 22 of the prosthesis socket 20. In principle, shorter or longer shafts 120 can be provided.

The dome bolt 15 is arranged on the inner side 22 by way of a bolt 150. The bolt 150 features an outer thread 151, which corresponds to the inner thread 141 of the dome nut 14. The outer thread 151 is only partially screwed into the inner thread 141. The bolt 150 joins a dome cap or the so-called dome 152, which is designed to be slightly curved or calotte-shaped or mushroom-shaped. From the outer edge of the dome 152, the back extends slightly inwards, said back facing towards the inner side 22 of the prosthesis socket 20, such that preferably only one support ring or one support ring surface is available. The dome 152, the bolt 150 and the dome nut 14 are designed to be able to conduct electricity. Potentials for stimulation caused by muscle activities are conducted by way of the dome 152 and the dome nut 14 via the contact tab 12, which is coupled with the dome nut 14 so it can conduct electricity, to a cable—not depicted—which is then connected to a plug. The detected electrical potentials of muscle activities are transmitted via the cable and the plug, for instance for evaluation purposes or for controlling a prosthesis component.

Figure 3:
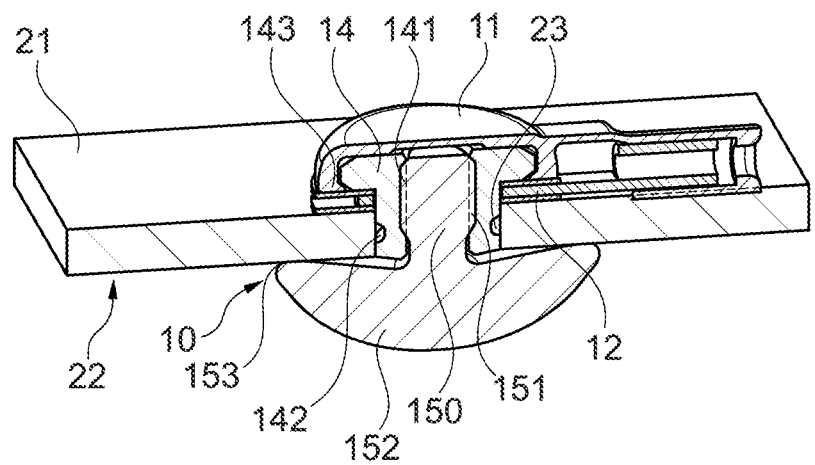
FIG. 3—a sectional view of a lead electrode after assembly.

FIG. 3 shows a sectional view of the assembled state. The dome bolt 15 is entirely bolted to the dome nut 14. The lower edge of the dome 152 lies on the inner side 22 of the prosthesis socket 20 and the pressure causes it to be pushed against the prosthesis socket 20, rendering it moisture-proof. A further sealing of the passage opening 23 is achieved by the sealing ring in the outer groove 142 and the two discs 13, which clamp the contact tab 12.

The assembly of the lead electrode 10 occurs following the drilling or other method of production of the passage opening 23 in the prosthesis socket 20. Preferably, the bolt 152 is initially inserted through the passage opening by way of the outer thread 151 of the dome bolt 15 and held in this position. The dome nut 14 with the attached discs 13, the contact tab 12 arranged between said discs and, where applicable, a sealing ring is pre-assembled. The cap 11 is not yet arranged above the dome nut 14. An inner hexagonal recess or a slit, for example, may be arranged in the dome nut 14, in order to be able to fix the lead electrode 10 to the wall of the prosthesis socket 20, such that is moisture-proof and can conduct electricity, with a single tool. The cap 11 is then clipped on and positively fixed by way of an undercut in the dome nut 14. The cable is inserted through the casing of the cable housing of the contact tab 12, thereby simply and quickly achieving an electric insulation from the outside. This type of electrode allows for a low structure height above the socket, especially on the outer side 21. The dome 152 enables rapid assembly of the electrode. A reversible assembly can be achieved via a screw connection; the sealing ring and the two discs 13 safeguard the dome nut 14 against an inadvertent detachment of the connection. The discs 13 may be designed to be crushing discs. The dome nut 14 can be pre-assembled with the electrical contact and the sealing ring; the discs 13 and the contact tab 12 are secured against inadvertent slipping by way of the sealing ring. The screw connection allows for an adjustment to different wall thicknesses of the prosthesis socket 20.

The above-named embodiments are applicable for both lead electrodes 10 that are fixed to a prosthesis socket 20 and for surface electrodes 100 that are mounted on a surface electrode arrangement 200, such as a sleeve or the like, which shall be described in the following.

Figure 4:
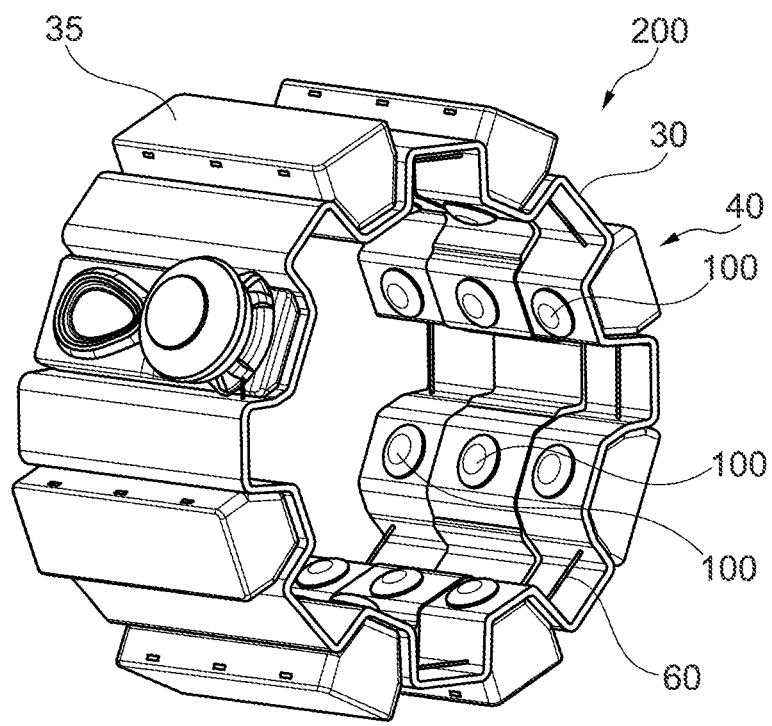
FIG. 4—a perspective depiction of a surface electrode arrangement with surface electrodes.

FIG. 4 shows a surface electrode arrangement 200, the surface electrodes 100 of which are constructed in the same way as the lead electrodes 10 in FIGS. 1 to 3. The surface electrode arrangement 200 is designed as a sleeve and comprises a support element, which is designed to be corrugated. The surface electrodes 100 are arranged on the corrugated projections of the support element 30, which face inwards, in order to guarantee secure contact with the skin. The linearly arranged surface electrodes 100, which have 3 poles, are arranged at an equal distance or for the most part at an equal distance from one another across the circumference of the support element 30, which is designed as a closed ring. Slight deviations in the distance of the electrodes or electrode lines across the circumference may be implemented. On the outer side of the support element 30, an amplifier 40 is allocated to each surface electrode 100, wherein the recorded myoelectric signals are amplified and, where applicable, pre-processed and transmitted inside said amplifier. Each amplifier 40 is arranged in an elongated housing 35 and may comprise its own energy storage system. A supply connection 50 is arranged in a recess—not depicted—on the outer side of the support element 30, by means of which energy can be supplied to the individual amplifiers 40. Furthermore, a common derivation of the surface electrode signals to a control unit can be achieved via the supply connection 50. A tensioning device 42 is also provided, by means of which the circumference of the sleeve or the support element 30 can be adjusted.

Due to the corrugated form of the support element 30, it is possible to achieve an elastic and radially expandable structure, such that the surface electrode arrangement 200 can be placed on limbs of varying diameters and circumferences. As a result, it is possible to use the surface electrode arrangement 200 within the scope of an initial treatment and initial evaluation of patients, without the need for the production of a custom-made prosthesis socket.

In the example of an embodiment shown, eight 3-pole surface electrode triplets are arranged on the support element 30. The support element 30 and thereby also the surface electrode arrangement 200 is, as described above, designed to be elastic in the circumferential direction and arranged in the axial direction, i.e. in the proximal-distal direction, or in the longitudinal direction of the linearly arranged surface electrodes 100 of an electrode triplet, such that it is not variable in length or it is rigid. As a result, it is possible to define a fixed distance between the surface electrodes 100 of an electrode triplet or two electrodes of an electrode pair. The surface electrode arrangement 200 is arranged on a limb such that it can be twisted and shifted, in order to be able to determine the optimal position of the surface electrodes 100 for deriving clear myoelectric signals.

Figure 5:
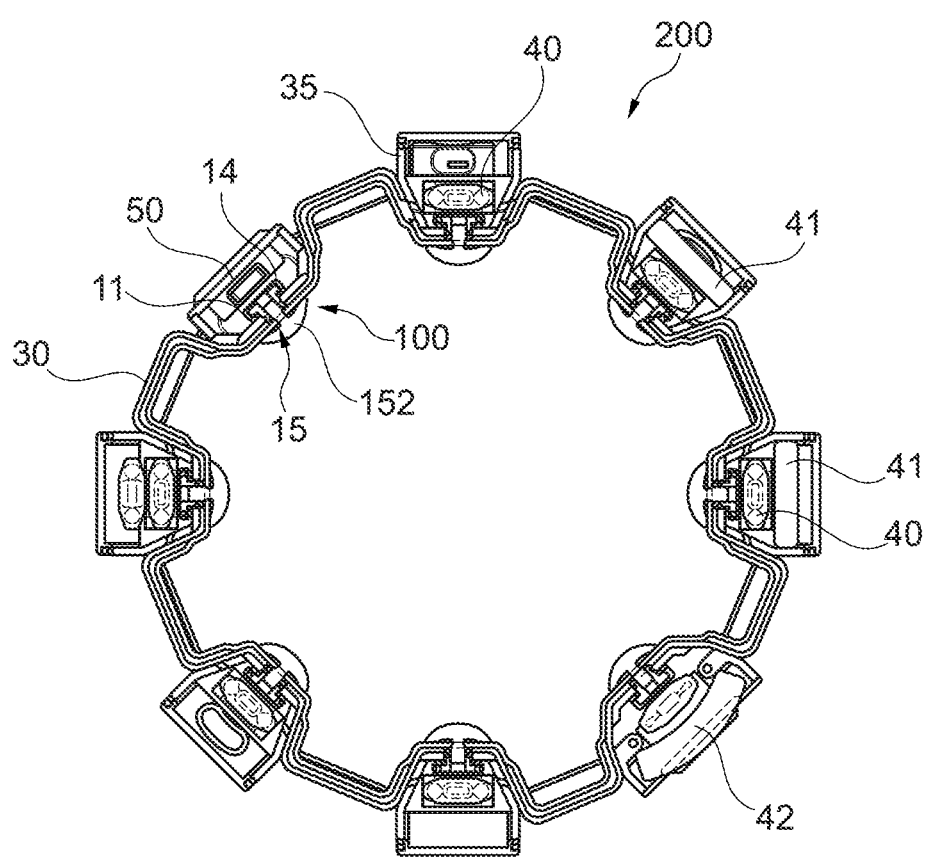
FIG. 5—a cross-sectional view of the surface electrode arrangement according to FIG. 4.

FIG. 5 shows a cross-sectional view of the surface electrode arrangement 200 device 200 according to FIG. 4. The individual surface electrodes 100 are constructed as dome bolts 15 with dome nuts 14, as in FIGS. 1 to 3. The total of eight rows of electrodes are arranged in pairs facing one another and spread across the circumference. In the sectional view, it is clear to see that energy storage systems 41 are only arranged in some of the amplifiers 40. An elastic cord or a strap 60 or a flexible cord that does not yield to tension may be arranged between the individual electrodes 100 along with the tensioning device 42, in order to increase the compression effect and to facilitate and enable a reset following an expansion.

Figure 6:
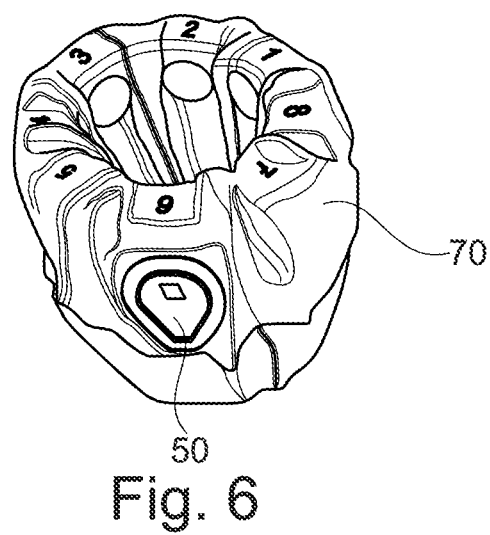
FIG. 6—a surface electrode arrangement with a replaceable cover.

FIG. 6 shows a perspective view of a surface electrode arrangement 200 with a cover 70 arranged around and pulled over it, wherein said cover may be made of a highly flexible fabric. The cover 70 is arranged on both the inner and outer side of the surface electrode arrangement and almost completely covers it. Only the domes 152 of the surface electrodes 100 on the inner side of the circular or sleeve-like support element 30 are free, so as to enable direct contact with the skin. Furthermore, on the outer side of the surface electrode arrangement 200, the supply connection 50 is free in order to convey energy and data from the amplifiers 40 to the surface electrodes 100, for example. The cover 70 is fixed to the support element 30 such that it can be detached. An undercut 153 is formed on the domes 152 via the slightly rounded shape of the mushroom-shaped heads, such that the fabric can be placed in the gap or undercut with the corresponding hole or the corresponding recess 71. The attachment on the outer side can be achieved via a velcro fastener or buttons or press studs, so that the cover 70 is easy to put on and take off again.

Markings in the form of numbers are provided on the front end of the surface electrode arrangement 200 in order to enable a clear allocation of the electrodes or electrode pairs across the circumference. This facilitates the signal evaluation and the respective signal can be allocated to a row of surface electrodes 100 or a pair of surface electrodes.

Figure 7:
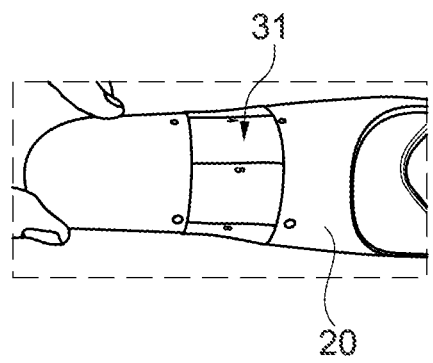
FIG. 7—a positioning aid.

A variation of the invention in FIG. 7 illustrates how, once found, a position of the surface electrodes 100 of a surface electrode arrangement 200 on a residual limb 1 can be transferred to a prosthesis socket 20. In the example of an embodiment, this occurs by way of a positioning aid 31, which is made of an elastic textile sleeve, on whose outer side markings are arranged at an equal distance from one other, e.g. in the form of consecutive numbers from 1 to 8. The distance of the markings from one another preferably changes in a uniform manner when the textile expands in order to adjust to the respective circumference of the limb. In an embodiment, the textile exhibits uniform expansion behavior in the circumferential direction. In this case, the width of the sleeve or the strap stipulates the optimal distance of the electrodes in the axial direction, i.e. in the proximal-distal direction, or along the longitudinal distance of the residual limb; the markings stipulate the distances of the electrodes in the circumferential direction. In FIG. 7, the positioning aid is arranged on a prosthesis socket 20. The markings can be used to indicate the respective positions of the electrodes and thus the location for a passage opening on the prosthesis socket 20. Instead of the markings, correspondingly placed holes may be provided in the positioning aid, said holes serving as a template for the optimal positions of the passage openings and therefore the electrodes. This type of variation is depicted in FIG. 8.

The surface electrodes 100 fixed on the support element and the lead electrodes 10 that are to be positioned on the prosthesis socket 20 are spread across the circumference and in the longitudinal direction of the residual limb such that they are almost equidistant from one another. In order to reduce the possibility of a decrease in the proposed distance of the electrodes from one another, stabilizing elements may be arranged in the longitudinal direction of the positioning aid 31, such that the positioning aid 31 can be expanded radially, but cannot be shortened axially. The support element of a surface electrode arrangement 200 may also be made of an elastic textile or comprise such a textile, and be equipped with stabilizing elements.

Figure 8:
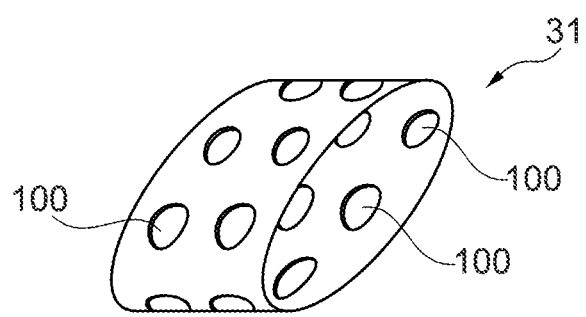
FIG. 8—a variation of a positioning aid.

FIG. 8 shows a variation of a positioning aid 31 with markings and/or holes or a surface arrangement 200 with surface electrodes 100. The surface electrode arrangement 200 or the positioning aid 31 is designed to be strap-shaped and not a closed ring. The surface electrode arrangement 200 or the positioning aid 31 may be placed around a limb and fixed. The diameter or the circumference is designed to be variable, for example by arranging a velcro fastener on the outer side so a surface electrode arrangement 200 can be arranged on residual limbs and positioning aids 31 on prosthesis sockets 20 of varying circumference or diameter.

Figure 9:
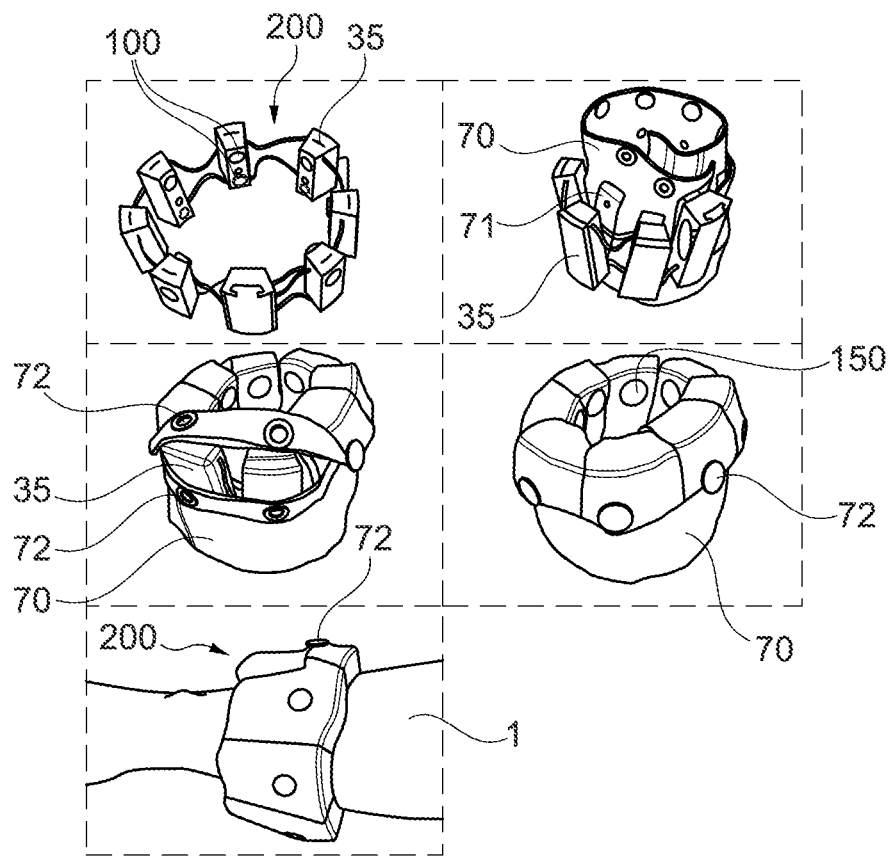
FIG. 9—a sequence for placing a surface electrode arrangement.

FIG. 9 shows the process of placing a surface electrode arrangement 200 on a patient. The top left of the diagram depicts a perspective view of the surface arrangement. The amplifiers 40 are arranged in the elongated housings 35, which also act as stabilizing elements. The surface electrodes 100 are arranged inside the housings at a distance from one another in the longitudinal direction of the housings 35. The individual amplifiers 40 in the respective housings 35 are connected via a cable; a cord 60 may be tensioned and released by way of a tensioning device 42 in order to be able to adjust the circularly arranged surface electrodes 100 or housings 35 of the surface electrode arrangement 200 with regard to their maximal circumference.

In the second image at the top right, the cover 70 is placed in the circular arrangement of the surface electrode arrangement. The cover 70 is designed as a tube or a sleeve and features recesses 71 that correspond to the domes 152, the domes 152 being inserted through said recesses. Sections of the cover 70 protrude at the proximal and distal ends, i.e. in the longitudinal direction, at the end of the sleeve 30. Once all the domes 152 have been inserted through the recesses 71, the sections of the cover 70 that protrude in the longitudinal direction are turned over so they end up on the outer side of the housings 35. This step is illustrated in the central left image in FIG. 9. Fastening elements 72 are arranged on the cover 70, which are designed as press studs in the example of an embodiment shown. Alternative fastening elements 72 may be provided, such as velcro fasteners or buttons. The fastening elements 72 are engaged in such a way that the outer side of the surface electrode arrangement 200 is completely encased by the cover 70. The fully assembled cover 70 on the surface electrode arrangement 200 is shown in the lower right image. The fastening elements 72 lie on the outer side of the surface electrode arrangement; the domes 152 are arranged on the inner side of the sleeve-like support element 30.

The lower left image in FIG. 9 depicts the surface electrode arrangement 200 with the cover 70 in place. The cover 70 may supply elastic restoring forces; it is also possible for the circumference to be set via the tensioning device 42 on one of the housings 35 of the surface electrode arrangement.

Figure 10:
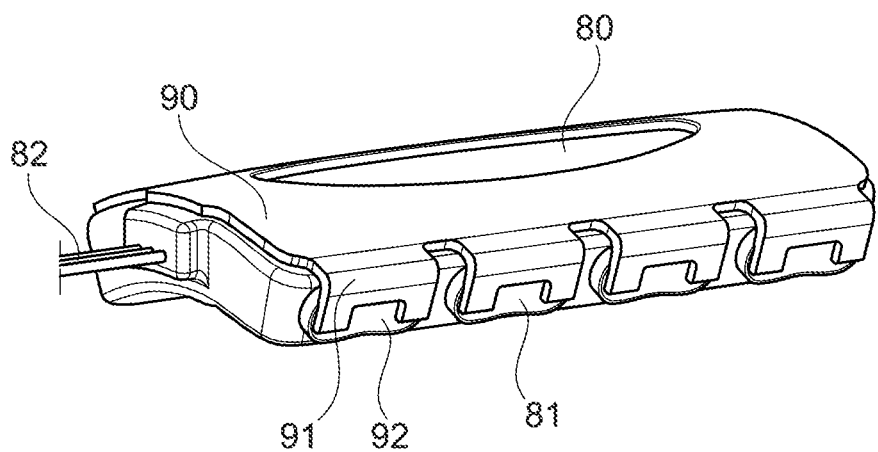
FIG. 10—a control unit with a safety element without a plug.

FIG. 10 shows a perspective depiction of a control unit 80 with a housing, on whose outer side plug sockets 81 are arranged, into which the plugs—not depicted—can be connected, said plugs being connected via cable to the surface electrodes 100 or the lead electrodes 10. In the example of an embodiment shown, the plug sockets 81 or sockets are arranged on opposite longitudinal sides of a flat, slightly curved housing. In the example of an embodiment shown, a total of eight plug sockets 81 are provided, four on each longitudinal side. The slight curvature is proposed in order to be able to fix the control unit 80 more easily to a prosthesis socket 20 or a patient. The control unit 80 features a cable outlet 82, by means of which the control unit 80 is coupled with a driven prosthetic component—not depicted—in order to transmit control signals to the respective drive on the basis of a selected control method. Based on the myoelectric signals received by the surface electrodes 100 or the lead electrodes 10, the respective drives are driven and activated or deactivated. The activation is executed with regard to adjustment speed, adjustment path and adjustment duration and/or strength.

A safety element 90 is allocated to the control unit 80, said safety element being fixed by way of clamping to the outer side of the housing of the control unit 80, wherein the outer side curves outwards. In the region of the plug sockets 81, the safety element 90 comprises clamps or tabs 91, which partially cover the opening of the plug socket 81. A recess 92 is provided in each clamp or tab 91 which acts as passage for the cable. To fix the plug connection of the surface electrodes 100 or the lead electrodes 10 to the control unit 80, the plugs 19 on the cables 18 of electrodes 10, 100 are inserted into the plug sockets 81. Once all the plugs have been inserted into the plug sockets 81, the safety element 90 is placed over the housing of the control unit 80 and clamped in place. The tabs or clamps 91 prevent the plugs from pulling out against the direction of insertion; however, the cables can still be essentially pulled through the recesses 92 in the tabs or clamps 91 to ensure that no kinks emerge. The safety element 90 provides a detachable, mechanical safeguarding against an inadvertent break in contact of the plugs.

Figure 11:
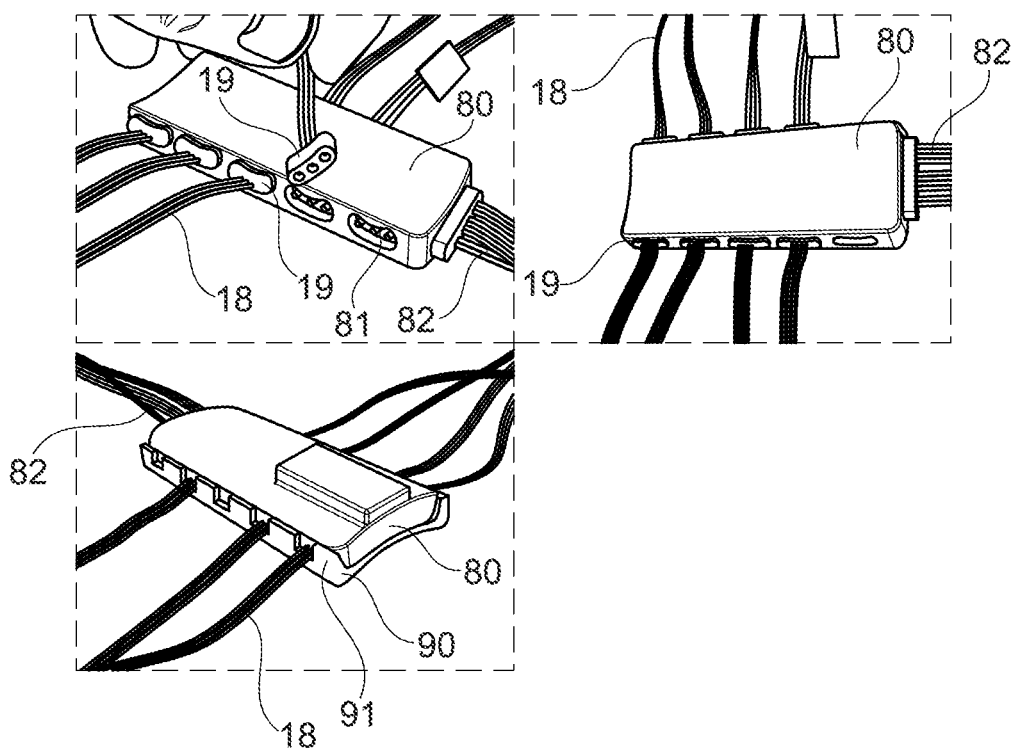
FIG. 11—a process for the assembly of plugs on a control unit with safety elements.

FIG. 11 shows a variation of the invention with the control unit 80 and a housing which, correspondingly with FIG. 10, features a total of ten plug sockets 81 on the narrow longitudinal sides of the housing, five on each side. In the upper left image of FIG. 11, several plugs 19 have already been inserted into the plug sockets 81. The plugs 19 are configured at 3-pole plugs, to which the cables 18 of the individual electrodes 10, 100 are fixed. In the upper left image of FIG. 11, seven plugs 19 have already been inserted into the plug sockets 81 of the control unit 80. In the upper right image, all plug connections of the surface electrodes 100 of the sleeve have been inserted in accordance with FIG. 4. The lower left image illustrates the secured image with eight inserted plugs 19, essentially straight cables 18 extending from said plugs and the safety element 90 with the clamps 91 and the recesses 92. Unlike in FIG. 10, in the example of an embodiment according to FIG. 11 the safety element 90 is arranged on the inner side of the housing of the control unit 80. The cable outlet 82 connects the control unit 80 to the prosthesis components that are to be controlled.

Figure 12:
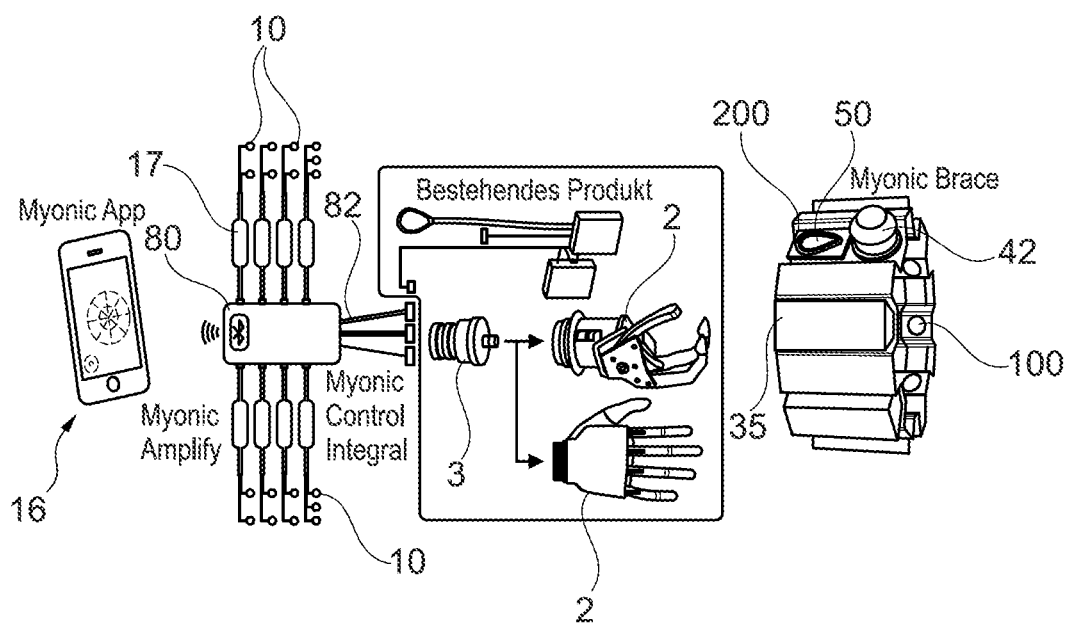
FIG. 12—a schematic depiction of a prosthesis system.

FIG. 12 shows a schematic depiction of the prosthesis system with a prosthesis component 2, which is designed in the form of an existing product. The prosthesis component 2 can be placed on a support 3. In the example of an embodiment shown, two different prosthesis components 2 can be selected: one is a simple gripping device that can be controlled via a dual channel control system. The gripping device can grip and release, such that a single drive has to be activated, reversed and stopped in order to be able to perform the desired activity. The lower prosthesis component 2 is a prosthetic hand featuring a number of driven prosthetic fingers, which have different drives, such that a considerably more complex control system is required in order to be able to execute a control using signals, especially electric signals, that have been derived from the patient. The support 3 is coupled with the control unit 80 via the cable outlet 82. The control unit 80 is connected to the lead electrodes 10 via plugs 19 and cables 18. The electrode pairs are shown, as is an electrode triplet with additional lead electrodes as ground.

An adapter 17 may be arranged between the lead electrodes 10 and the control unit 80, by means of which signals from the lead electrodes 10, which are actually suitable and proposed for controlling on the basis of pattern recognition, are converted into dual channel control signals that can be used to control the gripping device on the basis of a dual channel control system. The control unit 80 may be coupled with an operating device 16, such as a computer, a tablet or a smartphone, via a wireless connection such as Bluetooth in order to configure the control. The operating device 16 may feature an authentication software that stipulates that only an authorized person can change the control on which the activation of the respective prosthesis component 2 is based.

Furthermore, the surface electrode arrangement 200 is shown as a further prosthesis system component, wherein said surface electrode arrangement is designed as described above and in particular can be placed around a residual limb 1 such that it can be shifted and twisted. The surface electrodes 100 on the inner side of the surface electrode arrangement 200 on the support element 30 can coupled with a control unit 80 via either cable 18 or plug 19 in order to receive information as quickly as possible concerning the electric signals that can and cannot be produced by a patient; this can be achieved without a finished prosthesis socket 2. On the basis of these electric signals recorded by the surface electrode arrangement 200, a decision is made either in the control unit 80 or in another evaluation unit or a controller as to whether a control via pattern recognition software or a dual channel control system is convenient and suitable. The surface electrode arrangement 200 can be brought into an optimized position, which is the most advantageous for the conducting of the myoelectric signals. The position and the allocation of the respective electrodes 100 of the electrode pairs, for example in the respective housing 35, are saved. The markings on the front end or the circumference of the support element 30 or the surface electrode arrangement 200 are used to determine which electrode 10 should be placed or arranged at which point. This positioning of the respective electrodes 10 or electrode pairs is then transferred to the final prosthesis socket 20. The transfer may be achieved either via a projection, the production of a template, a positioning aid 31 or the superimposition of the selected position onto a diagram, so that during the production of the prosthesis socket 20, the orthopedic technician knows where each passage opening 23 should be arranged for the purpose of fixing and positioning the lead electrode 10.

Figure 13:
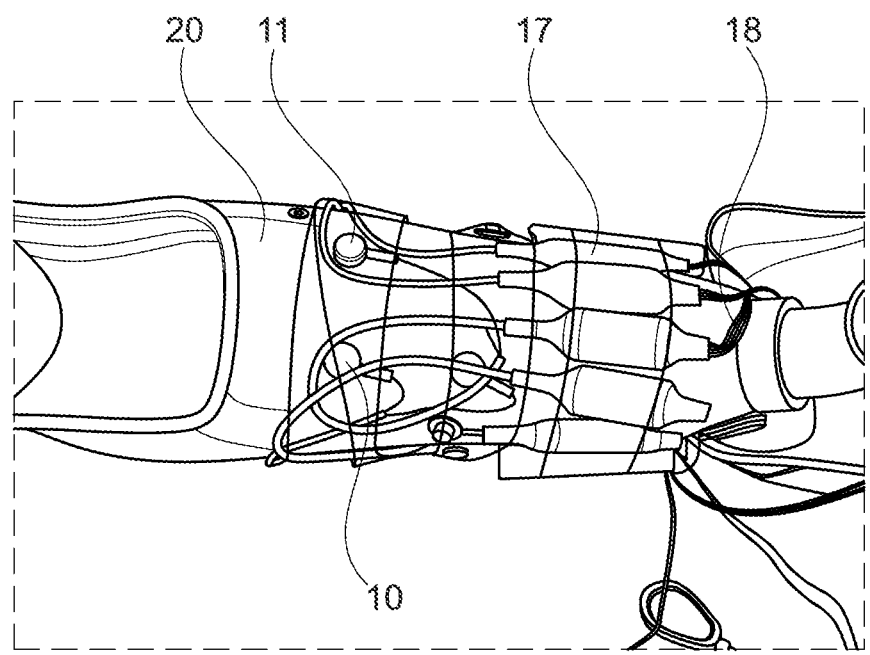
FIG. 13—a partial view of a complete prosthesis.

FIG. 13 shows the final arrangement of the lead electrodes 10 with the caps 11 on the prosthesis socket 20. The lead electrodes 10 are coupled with the control unit 80—not depicted—via the cables 18 and an adapter 17. The control unit in turn supplies the prosthesis component 2—not depicted—, which is fixed to the distal end of the prosthesis socket 20, with the corresponding commands the for respective drive.

The invention claimed is:

1. A method for configuring a myoelectrically controlled prosthetic system with a prosthesis socket and several lead electrodes for recording electric muscle activities, the method comprising:

placing a surface electrode arrangement comprising several surface electrodes around a circumference of a residual limb;
recording electric muscle activity in muscles of the residual limb as electromyographic signals, the activity being recorded by the surface electrodes;
evaluating the myoelectric signals with regards to a distinctness of the signals;
selecting a control procedure that is to be used to control the prosthesis system, based on the evaluation of the distinctness of the signals;
fixing the lead electrodes to the prosthesis socket;
undertaking a selection and definition of the control procedure; and
selecting a dual channel control system as the control procedure, identifying the two most easily distinguishable myoelectric signals, and indicating the position of the corresponding electrodes on the residual limb in an indicator device.

2. The method according to claim 1, further comprising designing the surface electrode arrangement to be independent from the prosthesis socket and placed separately from the prosthesis socket.

3. The method according to claim 1, further comprising arranging the surface electrode arrangement on the residual limb such that the surface electrode arrangement can be at least one of shifted and twisted.

4. The method according to claim 1, further comprising arranging the surface electrodes at an equal distance or at least at an equal distance from one another around the residual limb.

5. The method according to claim 1, further comprising evaluating the distinctness of the myoelectric signals of the surface electrodes on the basis of at least one of amplitude, duration, frequency and range.

6. The method according to claim 1, further comprising automatically executing the selection of the control procedure in a control unit on the basis of specific criteria.

7. The method according to claim 1 further comprising transmitting the position of the surface electrodes by a positioning aid from the residual limb to the prosthesis socket.

8. The method according to claim 7, wherein the position of the lead electrodes is indicated on the prosthesis socket, projected on the prosthesis socket or transferred onto the prosthesis socket by way of a positioning instruction.

9. The method according to claim 1, further comprising at least one of shifting and twisting the surface electrode arrangement on the residual limb into an end position, in which at least two signals can be detected, and the lead electrodes are fixed to the prosthesis socket correspondingly to the end position.

10. The method according to claim 1, further comprising fixing the lead electrodes to the prosthesis socket via a dome bolt connection.

11. The method according to claim 1, further comprising connecting the lead electrodes to a control unit via cables and mechanically securing the lead cables from becoming detached by way of a safety element.

12. A prosthesis system, comprising:
a prosthesis socket, which can be arranged on a residual limb;
several lead electrodes for recording electric muscle activities;
a control unit that is connected to the lead electrodes;
a driven prosthesis component, which is fixed to the prosthesis socket and coupled with the control unit; and a surface electrode arrangement with several surface electrodes, which are configured to be arranged around a circumference of a residual limb, wherein the surface electrode arrangement is configured to be arranged on the residual limb such that the surface electrode arrangement can be at least one of shifted and twisted, wherein at least one of the surface electrodes and lead electrodes are designed as a dome bolt with a dome nut and are bolted to the surface electrode arrangement or the prosthesis socket;

wherein the control unit is connected to the lead electrodes or surface electrodes via plugs such that the control unit can be detached, and wherein an adapter is arranged between the control unit and the plug for converting pattern recognition signals into dual channel control signals.

13. The prosthesis system according claim 12, wherein the surface electrode arrangement is designed to be a closed, circular strap.

14. The prosthesis system according claim 12, wherein the surface electrode arrangement is designed to be elastic in a circumferential direction.

15. The prosthesis system according to claim 12, wherein the surface electrodes are arranged in a circumferential direction at an equal distance or at least at an equal distance from one another on the surface electrode arrangement.

16. The prosthesis system according to claim 12, wherein at least one of the surface electrode arrangement and a positioning aid features at least one stabilizing element that extends in a proximal/distal direction.

17. The prosthesis system according to claim 12, wherein a replaceable cover is arranged on the surface electrode arrangement.

18. The prosthesis system according claim 17, wherein recesses for surface electrodes are designed in the cover.

19. The prosthesis system according to claim 12, wherein markings are arranged on at least one of a positioning aid and a replaceable cover.

20. The prosthesis system according to claim 12, wherein the dome bolt comprises an undercut and a passage spot is sealed against moisture.

21. The prosthesis system according to claim 12, wherein at least one cable is fixed to the prosthesis socket or the surface electrode arrangement such that the at least one cable can be detached and is in electrical contact with the lead electrode or the surface electrode.

22. The prosthesis system according to claim 12, wherein the plugs are mechanically secured against becoming detached by way of a safety element.

* * * * *